United States Patent [19]

Maddess

[11] Patent Number: 5,065,767
[45] Date of Patent: Nov. 19, 1991

[54] METHOD FOR USE IN DIAGNOSIS OF GLAUCOMA

[75] Inventor: Teddy L. Maddess, Kaleen, Australia

[73] Assignee: The Australian National University, Australia

[21] Appl. No.: 398,593

[22] Filed: Aug. 25, 1989

[30] Foreign Application Priority Data

Aug. 26, 1988 [AU] Australia .............................. PJ0049

[51] Int. Cl.$^5$ .......................... A61B 3/02; A61B 5/00
[52] U.S. Cl. ................................... 128/745; 351/222; 351/239; 351/246
[58] Field of Search .............. 128/745; 351/221, 222, 351/239, 242, 243, 246

[56] References Cited

U.S. PATENT DOCUMENTS

| | | | |
|---|---|---|---|
| 4,365,873 | 12/1982 | Ginsburg | 351/239 |
| 4,493,539 | 1/1985 | Cannon, Jr. | 128/745 |
| 4,634,243 | 1/1987 | Massof et al. | 351/243 |
| 4,676,611 | 6/1987 | Nelson et al. | 128/745 |
| 4,706,686 | 11/1987 | Levinson | 128/745 |
| 4,832,480 | 5/1989 | Kornacker et al. | 351/246 |

FOREIGN PATENT DOCUMENTS 2433580  2/1975  Fed. Rep. of Germany ...... 128/745

OTHER PUBLICATIONS

Kelly, *Journal of the Optical Society of America*, "Freq. Doubling in Visual Responses", vol. 56, p. 1628+, 1966.
Kelly, *Journal of the Optical Society of America*, "Non-Linear Visual Responses to Flickering Sinusoidal Gradients", vol. 71, p. 1051+, 1981.
Quigley et al., *Investigative Opthalmology and Visual Science*, "Chonic Glaucoma Selectively Damages Large Optic Nerve Fibers", vol. 28, p. 913, 1987.
*Journal of the Optical Society of America*, vol. 56, p. 1628, 1966.
*Journal of the Optic Society of America*, vol. 71, p. 1051, 1981.
*Investigative Opthalmology and Visual Science*, vol. 28, p. 913, 1987.

*Primary Examiner*—Lee S. Cohen
*Assistant Examiner*—K. M. Pfaffle
*Attorney, Agent, or Firm*—Sughrue, Mion, Zinn, Macpeak & Seas

[57] ABSTRACT

Existing techniques for diagnosis of glaucoma, namely observation of a scotoma, measurement of intraocular tension and assessment of color vision defects have drawbacks. The present invention overcomes those drawbacks by a psychophysical test in which a sinusoidal grating pattern is presented to a subject with the contrast of the pattern modulated at a frequency in the range from about 10 Hz to about 50 Hz, so that the subject can observe a frequency-doubled pattern of the grating. The contrast of the pattern is then reduced until a threshold value is reached, at which value the frequency-doubled pattern is no longer observed. The threshold value is then compared with the threshold value for persons of normal vision. A higher than normal threshold value indicates that the subject may be suffering from glaucoma. Persons with well-developed glaucoma have threshold values that are approximately twice the threshold value of a person with healthy vision. The pattern is conveniently established on the screen of a cathode ray tube, controlled by a programmed microprocessor.

8 Claims, 1 Drawing Sheet

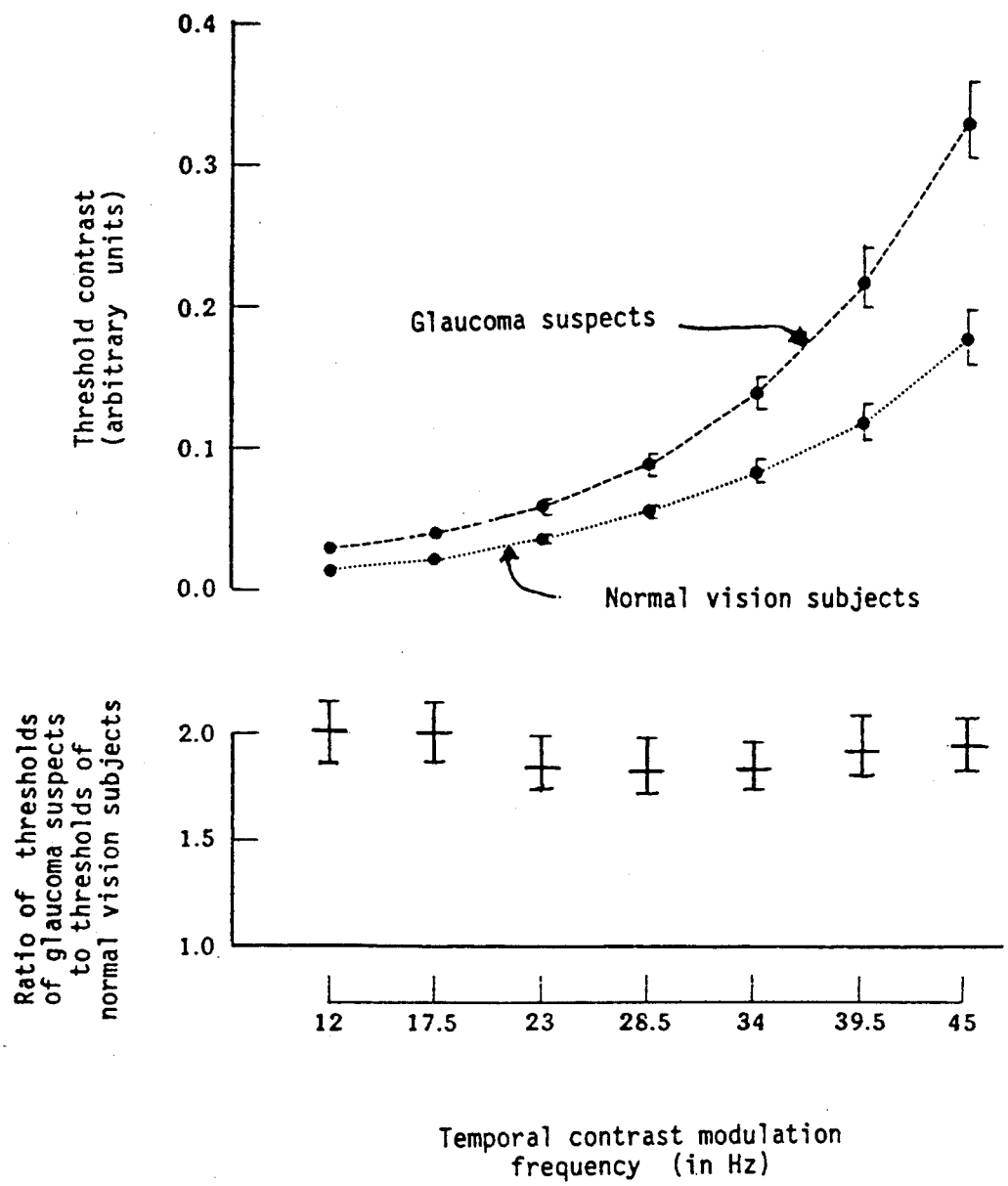

METHOD FOR USE IN DIAGNOSIS OF GLAUCOMA

TECHNICAL FIELD

This invention concerns the detection of glaucoma. More particularly, it concerns a method and apparatus whereby a person suffering from glaucoma can be diagnosed as such before the disease reaches the stage where the prospects for successful treatment are poor and irreversible blindness is almost inevitable.

BACKGROUND TO THE INVENTION

In the eye, the final stage of image processing in the retina is performed by retinal ganglion cells. The axons of the ganglion cells project out of the eye to form the optic nerve. Glaucoma, which produces irreversible blindness if not treated early enough, destroys these ganglion cells. A typical "early" sign of glaucoma is the loss of a portion of the peripheral visual field, referred to as "scotoma". Unfortunately, by the time a scotoma is detected, the disease has reached a stage where treatment is unlikely to be successful. Another indication of glaucoma is the presence of "cupping" of the optic disc.

One approach that has been used to detect glaucoma at an earlier stage than when a scotoma has developed is to test the intraocular tension of a patient. A symptom of glaucoma is the increase of intraocular tension. Tests of intraocular tension, however, usually involve the use of drugs, are time consuming, and are unpleasant for the patient. Moreover, in the early stages of glaucoma, an increased intraocular tension occurs only transiently in the morning and in the evening, and the susceptibility of patients to pressure damage as a result of increased intraocular tension varies. Moreover, some glaucoma patients do not exhibit intraocular tensions above about 21 mm of mercury (such patients have what is called "low-tension glaucomas"). Thus testing the intraocular tension of a person is not a reliable method for the early detection of glaucoma.

Another proposal for the early detection of glaucoma has involved the assessment of colour vision defects. Simple tests of colour vision defects, however, have shown a lack of correlation between the defects noted and the presence of optic disc cupping. More complex tests of colour vision defects involving anomaloscopy are too difficult for clinic use. Moreover, these tests cannot differentiate between colour vision defects caused by glaucoma and colour deficits resulting from amblyopia and optic neuritis. In addition, it has been reported that up to 25 percent of patients who have glaucomatous scotoma exhibit no colour deficit. Thus assessment of colour deficits in a person's vision is not a reliable method of detecting glaucoma in its early stages, even if it should become practical to perform detailed tests clinically.

DISCLOSURE OF THE PRESENT INVENTION

The prime object of the present invention is the provision of a non-invasive, easy to perform, reliable test for glaucoma, which enables the disease to be detected at its early stages.

To achieve this objective, the present invention utilises a pattern recognition phenomenon that is believed to be affected by the number of large ganglion cells present in the retina.

In 1966, D. H. Kelly reported, in his paper entitled "Frequency doubling in visual responses" (which was published in the *Journal of the Optical Society of America*, Volume 56, page 1628, 1966), that when sinusoidal gratings with spatial frequencies below 1 cycle per degree are modulated so that the contrast between the bars or striations of the pattern is varied at rates higher than 10 Hz, the gratings appear as spatial frequency-doubled sinusoids to persons of normal vision. D. H. Kelly's subsequent work (reported in his paper entitled "Non-linear visual responses to flickering sinusoidal gratings", which was published in the *Journal of the Optical Society of America*, Volume 71, page 1051, 1981) has shown that this second-harmonic distortion of the human visual response is due to the optical pathway between the eye and the brain having both a linear component and a non-linear component. Ganglion cells are known to be of two types, namely "M" type ganglion cells and "P" type ganglion cells, each of which respond to visual stimuli. However, the P type ganglion cells respond in a sluggish manner and do not contribute to the production of the images with which the present invention is concerned. The M type cells consist of larger "y-type" ganglion cells (usually designated "$M_y$" cells) and smaller "x-type" ganglion cells (usually designated "$M_x$" cells). Each type of cell is distributed uniformly over the back of the retina. There are significantly fewer $M_y$ cells than $M_x$ cells. Recent work has shown that the $M_y$ cells are responsible for the non-linear component of the optical pathway, that the $M_x$ cells control its linear component, and that the $M_y$ cells are the more important in the image forming process. Recent work has also indicated that patients having glaucoma also suffer a diffuse, and not just a localised, loss of ganglion cells. There is also data available, from experimental work with primates, to show that the $M_y$ cells are affected first at the onset of glaucoma-see the paper by H A Quigley et al, entitled "Chronic glaucoma damages large optic nerve fibres", which was published in *Investigative Opthalmology and Visual Science*, Volume 28, page 913, 1987.

The present inventor hypothesised that, if this latest work is correct, (a) a diffuse loss of ganglion cells over the retina, although affecting both $M_x$ and $M_y$ cells, would have a greater effect on the non-linear component of the optical pathway because the $M_y$ cells are relatively few in number, and thus glaucoma sufferers will have a different visual response to intensity modulated patterns from persons with normal vision; in particular, the glaucoma sufferer should find it more difficult than a person of normal vision to detect the frequency doubled sinusoids noted above;

(b) the different visual response should be exhibited at an early stage of glaucoma—well before the loss of ganglion cells is sufficient to produce a scotoma; and (c) the different visual response should not be exhibited by patients suffering from amblyopia or optic neuritis.

Tests performed with seventeen persons having normal vision and twenty-seven glaucoma suspects have shown that the different visual responses are exhibited, and that glaucoma sufferers require a greater contrast between the striations of the grating pattern before they can see the frequency-doubled sinusoid pattern.

It should be noted that throughout this specification (including the claims), the term "contrast" is used in the technical sense, and is defined by the relationship $$\text{contrast} = \frac{I_{max} - I_{min}}{I_{max} + I_{min}}$$

where $I_{max}$ is the intensity of the maximum density of the striations in the grating pattern and $I_{min}$ is the intensity of the minimum density of the striations in that pattern.

Thus, according to the present invention, a method of testing a person to determine the presence of glaucomatous destruction of ganglion cells in a retina of that person comprises the steps of:

(a) monocularly presenting the person with a sinusoidal grating pattern having generally elongate striations, the contrast of the grating pattern being modulated at a frequency in the range of from about 10 Hz to about 50 Hz, the contrast of the grating pattern being such that the person can observe a frequency-doubled grating pattern;

(b) reducing the contrast of the grating pattern until a contrast value at which the frequency-doubled pattern is no longer observed is attained; and (c) comparing the attained contrast value at which the frequency-doubled pattern is no longer observed with the highest contrast value at which the frequency doubled pattern is no longer observed by persons of normal vision.

Preferably the frequency of modulation of the contrast of the pattern is in the range of from about 20 Hz to about 50 Hz, and more preferably in the range of from 23 Hz to 45 Hz. Since it is desirable to use this test to detect glaucoma at its very early stages, it is important to carry out with precision the determination of the threshold value or level of the contrast at which the frequency-doubled pattern is observed. Accordingly, one of two alternative techniques for this purpose is preferably adopted.

The first of these alternative techniques is a multiple staircase, two alternative, forced-choice procedure involving the steps of (i) adopting a first contrast value for the grating pattern, then causing the grating pattern to be moved slowly in a direction at right angles to the elongate direction of the striations of the grating pattern, and checking that the person can identify the direction of movement of the observed pattern;

(ii) reducing the contrast of the grating pattern by a predetermined proportion of the first contrast level;

(iii) causing the grating pattern to move slowly in a direction at right angles to the elongate direction of the striations of the pattern, and asking the person to identify the direction of movement of the observed pattern;

(iv) if the person correctly identifies the direction of movement of step (iii), repeating steps (ii) and (iii);

(v) if the person incorrectly identifies the direction of movement of step (iii), increasing the contrast of the grating pattern by a second predetermined amount, then repeating step (iii);

whereby a series of contrast values or levels at which the person fails to observe the direction of movement of the observed pattern, and thus fails to observe a frequency doubled pattern, is obtained, an average value of the series of contrast values being adopted as the threshold contrast value at which the person no longer observes a frequency doubled pattern of the grating.

The second alternative technique involves a steady downward adjustment of the contrast until the person determines the level at which the frequency-doubled grating pattern just disappears (at this point, some trace of flicker is usually still seen).

Glaucoma sufferers and suspects have consistently shown a much higher contrast threshold for the disappearance of the observed frequency-doubled grating pattern.

The present invention also encompasses apparatus for performing the above-noted tests, comprising a cathode ray tube or an equivalent visual display unit, by which a sinusoidal grating pattern can be established, which can be cyclically modulated in contrast, which is adjustable for movement of the striations of the pattern orthogonally relative to the elongate direction of the striations, and which has an adjustable contrast. A visual display unit with a programmed microcomputer has been used to test the present invention.

To demonstrate the efficacy of the present invention, an example of its use will now be described with reference to the accompanying drawing, which is a graphical representation of the variation of contrast level at the threshold of observation of the aforementioned frequency doubled pattern with the modulation frequency of the temporal contrast, for persons having normal vision and for suspected glaucoma sufferers.

EXAMPLE OF THE EFFICACY OF THE INVENTION

A group of people comprising 17 persons with normal vision and 27 persons who were glaucoma sufferers were tested using the method of the present invention. Each person's threshold contrast level was measured using each of the alternative techniques for threshold determination, and using modulation frequencies of 12 Hz, 17.5 Hz, 23 Hz, 28.5 Hz, 34 Hz, 39.5 Hz and 45 Hz (except that in the later experiments, the modulation frequencies of 12 Hz and 17.5 Hz were not used—partly to reduce the length of the experiment and partly because it was often not possible for even the normal sighted subjects to pick the direction of movement of a frequency-doubled pattern at these frequencies).

The equipment used for the testing was a Joyce Electronics cathode ray tube with a white phosphor screen, adjusted to a mean luminance of 297 candelas per square meter. For a number of the persons tested, the mean luminance was reduced to (a) 29.7 candelas per square meter and (b) 2.97 candelas per square meter. With each of these persons, the test results at the lower mean luminances were the same as those obtained with the mean luminance of 297 candelas per square meter.

The sinusoidal grating pattern was established, using known techniques, by Joyce Electronics GR SYS2-02A display driver, driven by a Gemini 280 microcomputer. Using this equipment, waveforms of 512 levels could have their contrast adjusted to 1 part in 4096. Temporal modulation of the pattern was sinusoidal and based on a single cycle lookup table of 1000 entries. The frame rate of the cathode ray tube was 100 Hz. Subjects viewed the patterns monocularly while their heads rested against chin and forehead supports. The viewing distance in each case was 72 cm, at which distance the displayed pattern subtended 12.8° in height and 16° in width.

When using the drifting pattern technique for determination of the threshold contrast level for observation of the frequency doubled pattern, the striations of the pattern were vertically oriented and were moved to either the left or the right of the cathode ray screen at a rate of 3.13° per second.

The reduction of contrast levels was to 80 percent of the previous contrast level, and when a subject failed to identify the direction of movement of the pattern, the contrast level was doubled. Between the testing steps, an unmodulated 0.5 cycles per degree grating was displayed on the cathode ray tube screen. In the experiments using this technique, each pattern was typically presented 26 times, and involved about 6 increases in contrast level (that is, the contrast level was reduced six times to a level at which the direction of movement of the pattern could not be determined by the subject). The average value of the determined thresholds was used as the threshold value for the subject.

Among the glaucoma suspects tested, two persons had been diagnosed as low-tension glaucomas, having never exhibited intraocular pressures above 21 mm of mercury. One of these two subjects had a ring scotoma in both eyes; the other had an arcuate scotoma in one eye. Another three subjects had arcuate scotomas in one eye only, these subjects having had intraocular tensions of, respectively, 26 mm Hg, 34 mm Hg and 42 mm Hg in the affected eyes, although at the time of testing, each of these subjects had their intraocular tensions controlled by topical use of TIMOPTAL (Trade Mark) to be about 13.5 mm Hg. The mean age of the normal vision group was 49.9 years. The mean age of the glaucoma suspects was 54.9 years.

Among the normal vision group, the contrast level at the threshold of observation of the frequency-doubled pattern was substantially the same for each subject, showing that there is a "normal threshold" for persons having healthy vision. The glaucoma suspects consistently exhibited a higher contrast level at the threshold of observation of the frequency-doubled pattern.

The results of the experiments are shown in graphical form in the accompanying drawing. As will be seen, the ratio of the threshold contrast levels of the glaucoma suspects to the threshold contrast levels of the normal vision group is approximately 2:1 for all the temporal modulation frequencies used.

Analysis of the variance in the results showed no significant age or gender effects in either of the threshold tests used.

Those skilled in the field of visual neuroscience will recognise that although specific examples of the use of the method of the present invention have been described above, modifications to the method can be made without departing from the present inventive concept.

I claim:

1. A method of testing a person to determine the presence of glaucomatous destruction of ganglion cells in a retina of that person, said method comprising the steps of:
    (a) monocularly presenting the person with a sinusoidal grating pattern having generally elongate striations, the contrast of the pattern being modulated at a frequency in the range of from about 10 Hz to about 50 Hz, the contrast of the grating pattern being such that the person can observe a frequency-doubled grating pattern;
    (b) reducing the contrast of the grating pattern until a contrast value at which the frequency-doubled pattern is no longer observed is attained; and
    (c) comparing said attained contrast value at which the frequency-doubled pattern is no longer observed with the highest contrast value at which the frequency-doubled pattern is no longer observed by persons of normal vision.

2. A method as defined in claim 1, in which the step of reducing the contrast of the grating pattern comprises providing a steady reduction of the contrast until the frequency-doubled pattern just disappears.

3. A method as defined in claim 2, in which the modulation frequency of the contrast of the grating pattern is in the range of from about 20 Hz to about 50 Hz.

4. A method as defined in claim 2, in which the modulation frequency of the contrast of the grating pattern is in the range of from 23 Hz to 45 Hz.

5. A method as defined in claim 1, in which the step of reducing the contrast of the grating pattern to attain the contrast value at which the frequency-doubled pattern is no longer observed is effected by a multiple staircase, two alternative, forced-choice procedure involving the steps of
    (i) adopting a first contrast value for the grating pattern, then causing the grating pattern to be moved slowly in a direction at right angles to the elongate direction of the striations of the grating pattern, and checking that the person can identify the direction of movement of the observed pattern;
    (ii) reducing the value of the contrast of the grating pattern by a predetermined proportion of said first contrast value; then
    (iii) causing the grating pattern to move slowly in a direction at right angles to the elongate direction of the striations of the pattern, and asking the person to identify the direction of movement of the observed pattern; then
    (iv) if the person correctly identifies the direction of movement of step (iii), repeating steps (ii) and (iii); or
    (v) if the person incorrectly identifies the direction of movement of step (iii), increasing the contrast of the grating pattern by a second predetermined amount, then repeating step (iii);
whereby a series of contrast values at which the person fails to observe the direction of movement of the observed pattern, and thus fails to observe a frequency doubled pattern, is obtained, an average value of said series of contrast values being adopted as said attained contrast value of the person.

6. A method as defined in claim 5, in which the series of contrast values at which the person fails to observe the direction of movement of the observed pattern comprises at least six contrast values.

7. A method as defined in claim 5, in which the modulation frequency of the contrast of the grating pattern is in the range of from 20 Hz to 50 Hz.

8. A method as defined in claim 5, in which the modulation frequency of the contrast of the grating pattern is in the range of from 23 Hz to 45 Hz.

* * * * *